United States Patent [19]

Djokić et al.

[11] Patent Number: 4,886,792

[45] Date of Patent: Dec. 12, 1989

[54] 10-DIHYDRO-10-DEOXO-11-AZAERYTHRONOLIDE A COMPOUNDS, METHODS AND INTERMEDIATES FOR THE MANUFACTURE THEREOF AND THEIR USE IN PHARMACEUTICALS AND IN THE MANUFACTURE THEREOF

[75] Inventors: Slobodan Djokić; Nevenka Lopotar; Gabrijela Kobrehel; Hrvoje Krnjević; Olga Carević, all of Zagreb, Yugoslavia

[73] Assignee: Sour Pliva, Yugoslavia

[21] Appl. No.: 180,491

[22] Filed: Apr. 12, 1988

[30] Foreign Application Priority Data

Sep. 3, 1987 [YU] Yugoslavia .......................... 1631/87
Jan. 18, 1988 [YU] Yugoslavia ............................. 85/88

[51] Int. Cl.$^4$ .................. A61K 31/395; C07D 273/01
[52] U.S. Cl. ..................................... 514/183; 540/467
[58] Field of Search ......................... 540/467; 314/183

[56] References Cited

FOREIGN PATENT DOCUMENTS 3012533 10/1980 Fed. Rep. of Germany ...... 540/467

*Primary Examiner*—Robert T. Bond
*Attorney, Agent, or Firm*—Pollock, Vande Sande & Priddy

[57] ABSTRACT

10-dihydro-10-deoxo-11-azaerythronolide A compounds and pharmaceutically acceptable acid addition salts of said compounds; methods and intermediates for the manufacture thereof; their use as antiinflammatory agents and processes for their preparation.

26 Claims, 3 Drawing Sheets

FIG. 1

FIG. 3

10-DIHYDRO-10-DEOXO-11-AZAERYTHRONO-LIDE A COMPOUNDS, METHODS AND INTERMEDIATES FOR THE MANUFACTURE THEREOF AND THEIR USE IN PHARMACEUTICALS AND IN THE MANUFACTURE THEREOF

The present invention relates to novel biologically active 10-dihydro-10-deoxo-11-azaerythronolide A compounds and their pharmaceutically acceptable acid addition salts, to methods and intermediates for the manufacture thereof and to their use in the manufacture of pharmaceuticals, especially antiinflammatory agents.

It has been known that numerous antibiotics, in addition to their basic antibiotic activity, also exhibit antiinflammatory properties. This characteristic, however, is most often not exploited in the treatment of inflammatory processes that are not induced by pathogenous microorganisms in order to avoid the too rapid resistance of the microorganisms and the possible resulting oversensitivity of the human organism to them. Therefore there has been a need for substances with antiinflammatory activity and no simultaneous antibiotic properties. These are most often compounds, whose chemical structure is not similar to that of antibiotics or—exceptionally, they may be obtained from antibiotics by means of chemical transformations. Thus there has been known D-penicillamine derived from penicillin (Abraham et al., Nature, 151, 107 (1943) and Ruiz-Torres, Arzneimittel-Forsch., 24, 914 (1974)).

In accordance with the known and assumed prior art, by means of the technique of Beckmann rearrangement of erythromycin A oxime followed by the reduction of the obtained erythromycin A imino ether, there was synthesized the 10-dihydro-10-deoxo-11-aza-erythromycin A (U.S. Pat. No. 4,328,334, 5/1982, Djokié et al.; J. Chem. Soc. Perkin Trans. 1, 1986, 1881). By the reductive methylation of the obtained amine in accordance with the modified Eschweiler-Clark process with formaldehyde in the presence of formic acid there was prepared the N-methyl-11-aza-10-deoxo-10-dihydroerythromycin A (GB patent 2,094,293 to Kobrehel and Djokié), a novel semisynthetic macrolide antibiotic of a 15-membered azalactone ring, which has been subjected to clinical tests under the generic name of azithromycin. The U.S. Pat. No. 4,464,527 (84) describes the process for obtaining the N-ethyl- and N-(n-propyl)-derivatives of 10-dihydro-10-deoxo-11-azaerythromycin A, which are also effective antibacterial agents.

The Applicant's own search of the prior art has revealed that 10-dihydro-10-deoxo-11-azaerythronolide A compounds and specifically their N-alkyl derivatives, their salts and/or O- and/or N,O-substituted alkanoyl derivatives have not been described as yet.

The first object of the present invention is a method for the manufacture of 10-dihydro-10-deoxo-11-azaerythronolide A compounds of the formula I wherein $R_1$ stands for a hydrogen atom, a lower alkyl group or a lower alkanoyl group, $R_2$, $R_3$, and $R_4$ have identical or different meanings and each stands for a hydrogen atom or a lower alkanoyl group, and optionally pharmaceutically acceptable acid addition salts thereof, which comprises (A) a one- or two-step hydrolysis of 10-dihydro-10-deoxo-11-alkyl-11-azaerythromycin A of the formula II wherein $R_1$ has the above meanings, $R_2'$ stands for a desosaminyl group, $R_3'$ stands for a cladinosyl group and $R_4'$ stands for a hydrogen atom, or (B) the reaction of 10-dihydro-10-deoxo-11-azaerythronolide A of the formula III with aliphatic aldehydes of the formula $$R_5-CHO \qquad (IV)$$

wherein $R_5$ stands for hydrogen or a lower alkyl group, preferably a $C_{1-3}$ alkyl group, in the presence of formic acid or hydrogen in the presence of a noble metal catalyst, and

(C) optionally subjecting the products obtained according to (A) or (B) to acylation with lower aliphatic acid anhydrides, preferably $C_{1-3}$ aliphatic acid anhydrides, and optionally converting the products obtained according to (A), (B) or (C) into pharmaceutically acceptable acid addition salts.

The hydrolysis according to the variant (A) of the present inventive method is performed in a single or in two steps. In the single-step embodiment the hydrolysis is achieved by means of highly concentrated inorganic acids in the presence of an inert solvent, e.g. chloroform, by means of heating under a reflux condenser for 16 to 60 hours, followed by the isolation of the product by means of extraction with the same solvent at a pH of 8 to 9.

The two-step hydrolysis comprises (i) the hydrolysis of the compound of the formula (II) with diluted inorganic acids at room temperature for 10 to 20 hours and the extraction of the obtained intermediate 6-O-desosaminyl-10-dihydro-10-deoxo-11-alkyl-11-azaerythromycin A of the formula V wherein $R_1$ and $R_2'$ have the above-defined meanings, in a non-solvent, such as methylene chloride, chloroform or diethyl ether, at a pH of 9 to 11, and (ii) the subsequent subjecting of the isolated intermediate(V) to hydrolysis as described above for the one-step method.

The method (B) of the present invention comprising the reductive alkylation of the compound (III) may be performed either ($B_1$) with formaldehyde in the presence of formic acid in an inert solvent, or ($B_2$) with aldehydes of the formula (IV) in the presence of hydrogen and a noble metal catalyst in an inert solvent.

According to the method ($B_1$) of the present invention the compound (III) is reacted with a 1–3 equimolar excess of formaldehyde in the presence of at least the identical quantity of formic acid, in an inert solvent, such as acetone, halogenated hydrocarbons, preferably chloroform, at reflux temperature of the reaction mixture for 2 to 8 hours, yielding the compound of the formula (I), wherein $R_1$ stands for a methyl group and $R_2$, $R_3$ and $R_4$ stand each for a hydrogen atom.

The method ($B_2$) comprises the reductive alkylation of the compound (III) with aldehydes of the formula (IV) with hydrogen in the presence of noble metal catalysts in an inert solvent, e.g. a lower alcohol such as methanol or ethanol (96% mass/mass). In practice, the reaction is performed with a 1–2 fold equimolar excess of the aldehyde and a 0.5 to equimolar quantity of the noble metal catalyst, preferably Pd/C (palladium-on-charcoal) (5% mass/mass). The reductive alkylation is performed at moderate temperature, e.g. 18° to 25° C., in a hydrogen atmosphere at the starting pressure of 10 to 30 bar for 2 to 10 hours. After the completed reaction the catalyst is filtered off and the product is isolated in a conventional manner, most suitably by the evaporation of the alcohol at reduced pressure and the isolation of the obtained product of the formula (I), wherein $R_1$ stands for a lower alkyl and $R_2$, $R_3$ and $R_4$ stand each for a hydrogen atom, by means of extracting the aqueous suspension with an inert organic solvent such as methylene chloride, chloroform or carbon tetrachloride.

The acylation may be performed by standard acylation methods (e.g. Jones et al, J. Med. Chem. 15, 631 (1972)).

A further object of the present invention are novel 10-dihydro-10-deoxo-11-azaerythronolide A compounds of the formula (IA)

wherein $R_1'$ stands for $R_1$ with the exception of a hydrogen atom and $R_2$, $R_3$ and $R_4$ have the above defined meanings, and pharmaceutically acceptable acid addition salts thereof.

The intermediates of the formula (V) are also novel compounds and constitute a further object of the present invention.

It should be noted that the compound of the formula (I), wherein $R_1$ stands for a hydrogen atom, per se pertains to the state of the art (see the afore-cited S. Djokié et al, J. Chem. Soc., Perkin Trans 1, 1986, 1881); the Applicants have, however, discovered a new, much improved method of the manufacture thereof according to the above-defined process (A) as well as its medicinal use, which has not been known as yet. The pharmaceutically acceptable acid addition salts of 10-dihydro-10-deoxo-11-azaerythronolide A compounds (I), which are also encompassed by the present invention, are obtained by the reaction of 10-dihydro-10-deoxo-11-azaerythronolide A compounds (I) with an at least equimolar quantity of a suitable acid, e.g. hydrochloric, hydrobromic, sulfuric, phosphoric, acetic, propionic, citric, succinic, benzoic acids etc., optionally in the presence of a solvent inert at the reaction conditions. The acid addition salts are isolated by filtration, provided they are not soluble in the applied inert solvent, or by means of precipitation achieved by the addition of a non-solvent for the corresponding salt, or by the evaporation of the solvent, most often by lyophilization.

Further objects of the present invention are pharmaceutical compositions comprising an effective amount of the compounds of the formula (I) as well as of their pharmaceutically acceptable acid addition salts, methods for treating human and animal inflammatory diseases and methods for the manufacture of pharmaceuticals comprising a compound of the formula (I).

Figure 1:
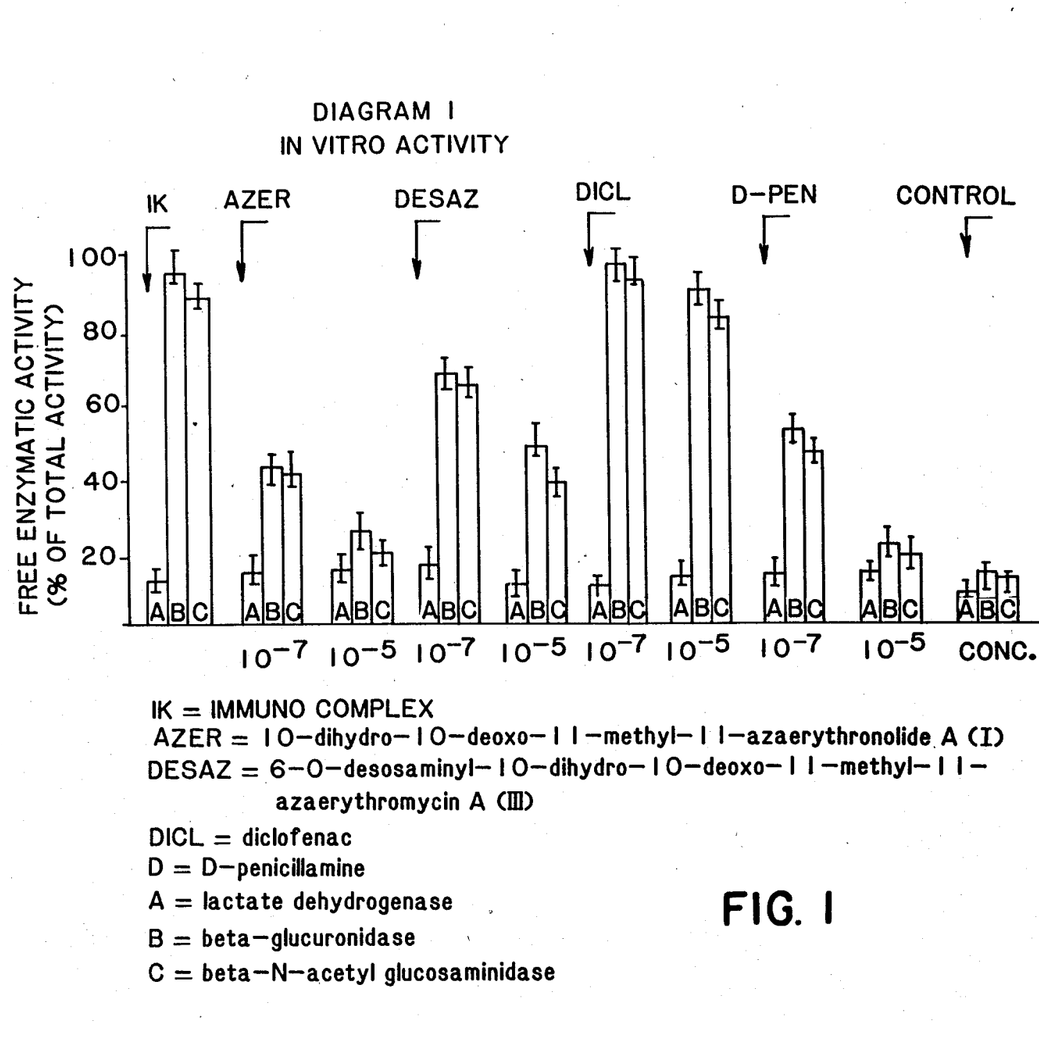
Figure 2:
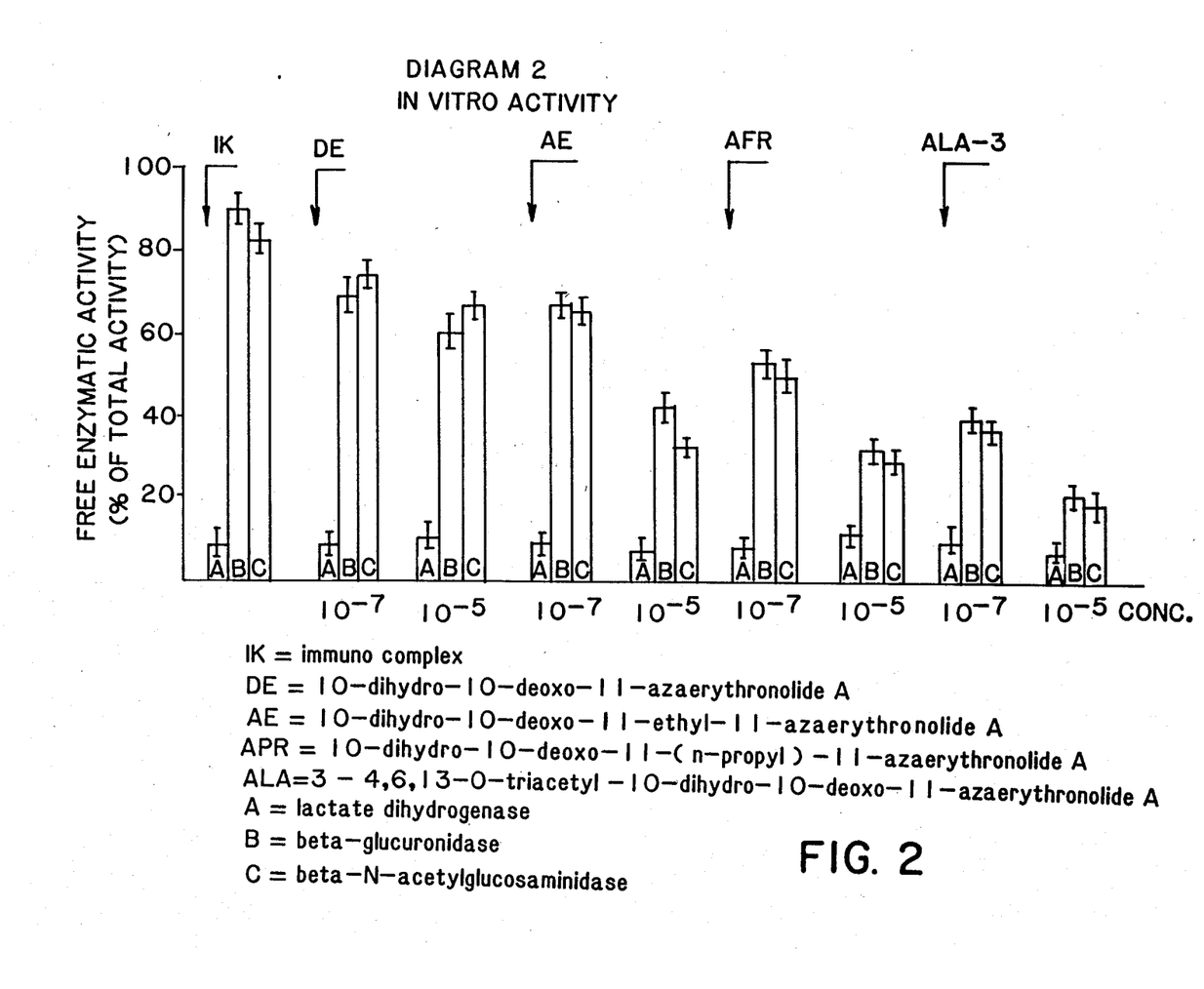

It has been found by in vitro and in vivo investigations that the compounds of said formula (I) exhibit a strong antiinflammatory activity. Their antiinflammatory properties were examined in vitro in comparison with diclofenac (DICL) and D-penicillamine (D-PEN), which are known antiinflammatory agents, on the model of extracellular release of lysosomic enzymes by human polymorphonucleic leukocytes (Weissman et aal, J. Exp. Med., 134, 149 (1971); Carevi, Agents and Actions 16, 407 (1985)) and the results are presented in the enclosed Diagrams 1 and 2.

It is evident from the Diagram 1 that the hydrolysis of azithromycin and the preparation of the corresponding 6-O-desosaminyl derivative (DESAZ) yields a product of a good antiinflammatory activity. In the concentration of $10^{-5}$ DESAZ shows an approximately equal activity as D-PEN in the concentration of $10^{-7}$. By the elimination of both sugar groups and by the synthesis of 10-dihydro-10-deoxo-11-methyl-11-azaerythronolide A (AZER) there is obtained a compound which strongly inhibits the extracellular release of lysosomic enzymes from polymorphonucleic leukocytes with a similar activity as D-PEN or—in a concentration of $10^{-7}$—with a stronger one.

In in vitro experiments DICL does not influence the extracellular release of enzymes. The in vitro activity of N-ethyl-(AE) or N-(n-propyl) derivatives is somewhat lower in comparison with AZER (Diagram 2). Yet the acylation of AZER with the acetic acid anhydride and the preparation of 4,6,13-triacetyl-10-dihydro-10-deoxo-11-methyl-11-azaerythronolide A (ALA-3) does not result in a substantial change in the in vitro activity.

Figure 3:
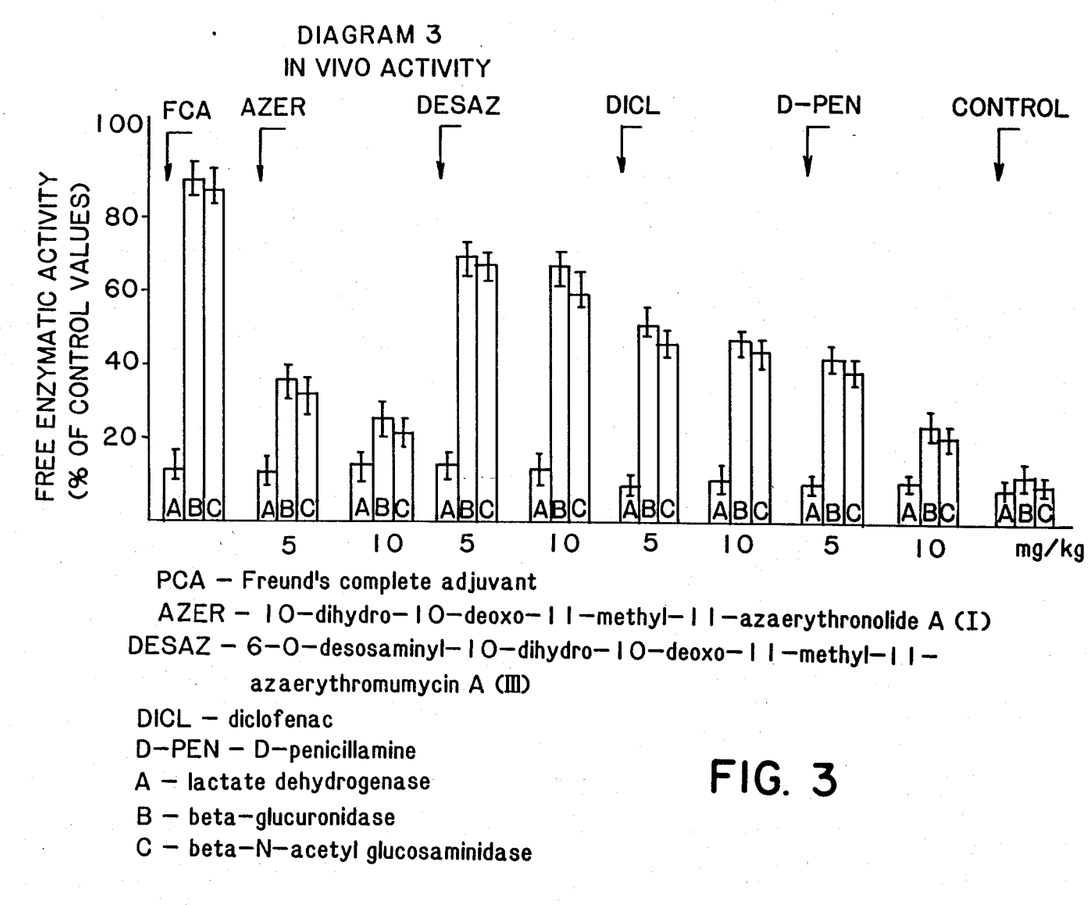

There were also performed in vivo investigations on a model of an adjuvant-induced arthritis in rats (Perason et al, Arthritis Rheum., 2, 440 (1959); Carevi, Publ. Yug. Acad. of Sci., 7, 415 (1985)). It can be concluded from the Diagram 3 that AZER significantly reduces the extracellular release of lyosomic enzymes into the synovial fluid of rats with the adjuvant-induced arthritis and that it exhibits a level of activity, which is equal to that of D-PEN and significantly higher that that of DICL. DESAZ showed a somewhat lower activity than D-PEN and DICL.

It is evident from the above results that the in vivo method is comparable with the in vitro assays. In these experiments the in vitro and in vivo investigated substances did not significantly influence the release of the enzyme lactate dehydrogenase (A), which proved that the cellular membrane was not significantly affected.

The antiinflammatory activity was also measured on the carrageenin-induced oedema of the rat's paw (Crunkhorn et al, Br. J. Pharm., 42, 392 (1971)).

The obtained results (30–40%) of the compounds (I) did not significantly exceed those of D-PEN and Acisal (35–45%). The activity of N-ethyl- and N-(n-propyl) derivatives (I) is on the level of the antiinflammatory activity of AZER. The O- and/or N,O-substituted compounds (I) and their salts, however, exhibited an improved activity in comparison with D-PEN.

The invention is illustrated but in no way limited by the following Examples.

EXAMPLE 1

10-dihydro-10-deoxo-11-azaerythronolide A

A mixture of 10-dihydro-10-deoxo-11-azaerythromycin A (100 g, 136.06 mmole), 6M HCl (750 ml) and $CHCl_3$ (380 ml) was kept at the boil under a reflux cooler for 16 hours. After cooling to ambient temperature the layers were separated and the aqueous layer was extracted by chloroform ($2 \times 100$ ml). By the addition of sodium lye the pH of the aqueous solution was adjusted to 5.0 and it was re-extracted by means of chloroform ($3 \times 100$ ml). The same procedure was repeated at a pH of 8.5 ($3 \times 250$ ml). The chloroform extracts of a pH 8.5 were dried over $K_2CO_3$ and evaporated at reduced pressure, yielding 53.77 g (94.2%) of the crude 10-dihydro-10-deoxo-11-azaerythronolide A. After the crystallization from diethyl ether (300 ml) there were obtained 34.45 g of the homogeous product (TLC, $C_6H_6$:$CHCl_3$:$CH_3OH$ 40:55:5, $NH_3$ $R_f$ 0.233) of the physical-chemical constants as described in J. Chem. Soc., Perkin Trans. 1, 1986, 1881.

EXAMPLE 2

10-dihydro-10-deoxo-11-methyl-11-azaerythronolide A

A mixture of azithromycin (II) (10 g, 13.35 mmole), 6M HCl (75 ml) and chloroform (38 ml) was kept at the boil under a reflux cooler for 48 hours. After cooling to ambient temperature the layers were separated and the aqueous layer was extracted with chloroform. The aqueous solution as adjusted to a pH of 5.0 by means of sodium lye and extracted again by means of chloroform. The same procedure was repeated at a pH of 8.5. The chloroform extracts were obtained at a pH of 8.5 and were concentrated in vacuo to a volume of about 10 ml and left standing to crystallize. After the filtration and drying there were obtained 4.7 g (81.2%) of the product, which was optionally recrystallized from chloroform. M.p. 208°–210° C.

|  |  | C | H | N |
|---|---|---|---|---|
| $C_{22}H_{43}NO_7$ | calc. | 60.94 | 10.00 | 3.23 |
|  | found | 60.72 | 9.63 | 2.96 |

EXAMPLE 3

6-O-desosaminyl-10-dihydro-10-deoxo-11-methyl-11-azaerythromycin A

A solution of azithromycin (10 g, 13.35 mmole) in 0.25M HCl (500 ml) was kept standing for 15 hours at ambient temperature. After the extraction with chloroform ($3 \times 75$ ml) the extracts were washed with 1M HCl and water. The combined aqueous layer was alkalized to a pH value of 10 by means of sodium lye and re-extracted by means of chloroform. The chloroform extracts were dried over $K_2CO_3$ and subsequently evaporated to dryness under reduced pressure. After the washing of the crude product with ether, there were obtained 6.9 g (87.8% theor.) of the product. M.p. 203°–205° C.

|  |  | C | H | N |
|---|---|---|---|---|
| $C_{30}H_{58}N_2O_9$ | calc. | 60.99 | 9.90 | 2.96 |
|  | found | 60.63 | 9.58 | 4.36 |

EXAMPLE 4

In accordance with the process described in Example 1, from 10 g of the product of Example 3 there were obtained 6.56 g (89.4%) of the product of Example 2.

EXAMPLE 5

10-dihydro-10-deoxo-11-methyl-11-azaerythronolide A

Into a solution of 10-dihydro-10-deoxo-11-azaerythronolide A (1 g, 2.38 mmole) in $CHCl_3$ (20 ml) there were charged 0.184 ml (2.38 mmole) of formaldehyde (36%) and 0.183 ml (4.77 mmole) of formic acid (98–100%) and the reaction mixture was refluxed under stirring for 8 hours. Then it was cooled to ambient temperature and left standing for 24 hours, whereupon the precipitated crystals were filtered off, washed with chloroform and dried, yielding 1.0 g (96.5%) of the crude 10-dihydro-10-deoxo-11-methyl-11-azaerythronolide A. The product was optionally crystallized from chloroform (TLC, $R_f$ 0.306).

M.p. 208°–210° C.

$^1$H NMR (CD$_3$OD): 2.351 ppm (N—CH$_3$)

EXAMPLE 6

10-dihydro-10-deoxo-11-ethyl-11-azaerythronolide A

Into a solution of 10-dihydro-10-deoxo-11-azaerythronolide A (5 g, 11.92 mmole) in ethanol (96%) (50 ml) there were charged acetaldehyde (7 ml, 120.5 mmole) and palladium-on-charcoal (5%) (2.5 g), whereupon the reaction mixture was hydrogenated under stirring for 10 hours at 20 bar. The catalyst was filtered off, washed with ethanol (20 ml) and the combined liquid phase was concentrated by evaporation at reduced pressure to a volume of about 30 ml. To the reaction mixture there were added water (100 ml) and CHCl$_3$ (50 ml), the pH was adjusted to 4.5 by the addition of 2M HCl, the layers were separated and the aqueous phase was re-extracted with chloroform (2×50 ml). The reaction step of extraction with chloroform was repeated after the alkalization to a pH value of 8.5 with an aqueous solution of sodium lye (3×50 ml), the combined chloroform extracts were dried over K$_2$CO$_3$ and evaporated at reduced pressure yielding 4.65 g (87.2%) of the crude 10-dihydro-10-deoxo-11-ethyl-11-azaerythronolide A. The obtained product was suspended in diethylether (10 ml), stirred for 1 hour at ambient temperature, filtered, the precipitate was washed with diethyl ether and dried, yielding 3.2 g of the chromatographically homogeneous product (TLC, $R_f$ 0.390), m.p. 204°–206° C.

EXAMPLE 7

10-dihydro-10-deoxo-11-(n-propyl)-11-azaerythronolide A

Into a solution of 10-dihydro-10-deoxo-11-azaerythronolide A (6 g, 14.30 mmole) in ethanol (96%) (60 ml) there were charged propione aldehyde (11.4 ml, 157.31 mmole) and palladium-on-charcoal (5%) (3.0 g), whereupon the reaction mixture was hydrogenated under stirring for 10 hours at 22 bar. The catalyst was filtered off, the filtrate was concentrated by evaporation at reduced pressure into a thick syrup, whereupon the product was isolated by pH-gradient extraction. Into the reaction mixture there were added water (100 ml) and dichloro methane (50 ml), the pH was adjusted to 4.5 with 2M HCl, the layers were separated and the aqueous layer was re-extracted with dichloro methane (2×50 ml). After the alkalization by means of an aqueous solution of sodium lye, the reaction step of extraction with dichloro methane was repeated at a pH of 8.5 (1×150 ml, 2×50 ml). The combined organic extracts at a pH of 8.5 were filtered, the filtrate was concentrated by evaporation at reduced pressure into a thick suspension, the separated crystals were filtered off, washed with dichloro methane and dried to obtain the chromatographically homogeneous title product (TLC, $R_f$ 0.415). Yield 4.3 g (65.2%). M.p. 212°–216° C.

EXAMPLE 8

4-O-acetyl-10-dihydro-10-deoxo-11-methyl-11-azaerythronolide A

Into a solution of 10-dihydro-10-deoxo-11-methyl-11-azaerythronolide A (5 g, 11.53 mmole) in pyridine (30 ml) there was added acetanhydride (30 ml) and the reaction mixture was left standing for 2 hours at ambient temperature. The acylation step was stopped by the addition of ice and the product was isolated by the extraction with chloroform at a pH of 9.0 (3×50 ml). The combined organic extracts were dried over K$_2$CO$_3$ and evaporated, yielding 3.4 g of the crude product. The suspending of the precipitate in diethyl ether (10 ml), the stirring of the suspension for 1 hour at ambient temperature and the filtration yielded 1.75 g (53.2%) of the title product, m.p. 187°–189° C. (TLC, $R_f$ 0.564).

IR(KBr): 1725 (C=O lactone and ester) and 1235 cm$^{-1}$ (OAc)

$^1$H NMR (CD$_3$OD): 2.343 (s, 3H, N—CH$_3$), 2.052 (s, 3H, 4—OAc) and 5.227 ppm (d, 1H, 4—H).

By means of the same process, with the exception that acetanhydride was substituted by propionic acid anhydride, there was prepared the corresponding 4-O-propionyl derivative.

EXAMPLE 9

4,6,13-O-triacetyl-10-dihydro-10-deoxo-11-methyl-11-azaerythronolide A

Into a solution of 10-dihydro-10-deoxo-11-methyl-11-azaerythronolide A (5 g, 11.53 mmole) in pyridine (50 ml) there was charged acetanhydride (50 ml) and the reaction mixture was left standing for 7 days at ambient temperature. The reaction was stopped by the addition of ice and the product was isolated by means of extraction with chloroform as described in Example 8. The combined organic extracts were dried over K$_2$CO$_3$, evaporated to dryness and chromatographed on a silica gel column by means of the system CH$_2$Cl$_2$/CH$_3$OH/NH$_4$OH 90:9:1.5. The combining of the fractions of the less mobile substance, the evaporation of the solvent and the drying of the obtained amorphous product yielded the 4,6,13-O-triacetyl derivative, m.p. 180°–182° C. ($R_f$ 0.337).

IR(KBr): 1740 (C=O, ester), 1715 (C=O, lactone) and 1240 cm$^{-1}$ (OAc)

$^{13}$C NMR (CDCl$_3$): 43.1 (q, N—CH$_3$), 173.5 (s, C=O lactone) and 170.2, 170.1 and 169.1 ppm (s, C=O acetates).

EXAMPLE 10

11-N,4,6-O-triacetyl-10-dihydro-10-deoxo-11-azaerythronolide A

From 10-dihydro-10-deoxo-11-azaerythronolide A (5.0 g, 11.9 mmole) and acetanhydride (50 ml) in pyridine (50 ml) there was obtained by acetylation according to the process described in Example 8 the crude 11-N,4,6-O-triacetyl-10-dihydro-10-deoxo-11-azaerythronolide A. The acetylation reaction was stopped after 24 hours, the product was isolated by means of conventional methods of extraction with chloroform and the obtained crude precipitate was purified by means of suspension in diethyl ether (50 ml), the stirring of the reaction suspension during 1 hour at ambient temperature and the filtration of the insoluble titled product. The yield: 4.08 g (68.3%).

M.p. 220°–223° C.
R_f 0.417
IR(KBr): 1715 (C=O, lactone and ester), 1605 (NAc) and 1240 cm$^{-1}$ (OAc).
$^1$H NMR (CD$_3$OD): 2.115 (s, 3H, N—Ac), 2.053 (s, 3H, 4—OAc) and 2.040 ppm (s, 3H, 6—OAc).

EXAMPLE 11

10-dihydro-10-deoxo-11-methyl-11-azaerythronolide A hydrochloride 10-dihydro-10-deoxo-11-methyl-11-azaerythronolide A (4.34 g, 10 mmole) was suspended in 25 ml of water, and under stirring, by the dropwise addition of 0.25N HCl during 1 hour, the pH was adjusted to 5.8. The clear reaction mixture was stirred for an additional hour at ambient temperature, filtered and lyophilized; yield 4.48 g (95.5%) of 10-dihydro-10-deoxo-11-methyl-11-azaerythronolide A hydrochloride.
$^1$H NMR (CD$_3$OD): 3.03 ppm (s, 3H, N—CH$_3$)
Analysis: Cl, calc. 7.54%, found 6.97%.

In an analogous manner, by the substitution of hydrochloric acid with hydrobromic, acetic, sulfuric, phosphoric, citric, benzoic etc. acids, there were prepared the corresponding salts of 10-dihydro-10-deoxo-11-alkyl-11-azaerythronolide A and N- and/or N,O-substituted derivatives thereof.

EXAMPLE 12

10-dihydro-10-deoxo-11-methyl-11-azaerythronolide A (method B)

According to the process of Example 5, starting from 10-dihydro-10-deoxo-11-azaerythronolide A (1 g, 2.38 mmole), formaldehyde (36%) (0.184 ml, 2.38 mmole) and formic acid (98–100%) (0.183 ml, 4.77 mmole) and reacting in acetone (20 ml), there were obtained 0.93 g (89.8%) of the title product.

EXAMPLE 13

10-dihydro-10-deoxo-11-ethyl-11-azaerythronolide A (method B)

According to the process as described in Example 1, starting from 10-dihydro-10-deoxo-11-ethyl-11-azaerythromycin A (5 g, 6.55 mmole) there were isolated 2.45 g (83.57%) of the title product with the same physical-chemical constants as described in Example 6.

EXAMPLE 14

10-dihydro-10-deoxo-11-(n-propyl)-11-azaerythronolide A

According to the process as described in Example 1, starting from 10-dihydro-10-deoxo-11-(n-propyl)-11-azaerythromycin A (5 g, 6.44 mmole) there were isolated 2.4 g (80.7%) of the title product of the same physical-chemical constants as described in Example 7.

EXAMPLE 15

6-O-desosaminyl-10-dihydro-10-deoxo-11-ethyl-11-azaerythromycin A 10-dihydro-10-deoxo-11-ethyl-11-azaerythromycin A (1 g, 1.31 mmole) was dissolved in 0.25M HCl (50 ml) and left standing for 16 hours at ambient temperature. The reaction mixture was then extracted with chloroform (3×10 ml) and the combined organic extracts were washed with 1M HCl and water. The combined aqueous layer was alkalized with an aqueous solution of sodium lye to a pH of 10 and re-extracted with chloroform (3×20 ml). The chloroform extracts were dried over K$_2$CO$_3$ and evaporated to dryness. After washing the crude product with ether there were obtained 0.7 g (88.4%) of the title product.
$^1$H NMR (CDCl$_3$): 2.24 ppm (s, 6H, N(CH$_3$)$_2$).

By means of the same process the hydrolysis of 6-O-desosaminyl-10-dihydro-10-deoxo-11-(n-propyl)-11-azaerythromycin A yielded the corresponding N-(n-propyl) derivative.

What is claimed is:

1. 10-dihydro-10-deoxo-11-azaerythronolide A compounds of the formula (IA)

wherein R$_1'$ stands for a lower alkyl group or a lower alkanoyl group, R$_2$, R$_3$ and R$_4$ have identical or different meanings and each stands for a hydrogen atom or a lower alkanoyl group, and their pharmaceutically acceptable acid addition salts.

2. The compound of formula (IA) as claimed in claim 1, wherein the lower alkyl group comprises 1 to 3 carbon atoms.

3. The compound of formula (IA) as claimed in claim 1, wherein the lower alkanoyl group comprises 1 to 3 carbon atoms.

4. A compound of formula (V)

wherein R$_1$ stands for a hydrogen atom, a lower alkyl group or a lower alkanoyl group and R$_2'$ stands for a desosaminyl group.

5. The compound of the formula (V) as claimed in claim 4, wherein the lower alkyl group comprises 1 to 3 carbon atoms.

6. The compound of the formula (V) as claimed in claim 4, wherein the lower alkanoyl group comprises 1 to 3 carbon atoms.

7. A method for the manufacture of 10-dihydro-10-deoxo-11-azaerythronolide A compounds of the formula (I)

wherein $R_1$ stands for a hydrogen atom, a lower alkyl group or a lower alkanoyl group, $R_2$, $R_3$, and $R_4$ have identical or different meanings and each stands for a hydrogen atom or a lower alkanoyl group, and optionally pharmaceutically acceptable acid addition salts thereof, which comprises hydrolysis of 10-dihydro-10-deoxo-11-alkyl-11-azaerythromycin A of the formula (II)

wherein $R_1$ has the above meaning, $R_2$, stands for a desosaminyl group, $R_3$, stands for a cladinosyl group and $R_4$, stands for a hydrogen atom.

8. The process of claim 7 wherein said hydrolysis is carried out in one step in a mixture of a concentrated inorganic acid in the presence of an inert solvent.

9. The process of claim 8 wherein said hydrolysis is carried out by heating under reflux.

10. The process of claim 8 wherein said solvent is chloroform.

11. The process of claim 7 wherein said hydrolysis is carried out in two steps which comprise hydrolysizing the compound of formula II in a dilute inorganic acid to thereby yield a 10-dihydro-10-deoxo-11-azaerythromycin A of the formula (V)

wherein $R_1$ stands for a hydrogen atom or a lower alkyl group and $R_2$, stands for a desosaminyl group; and wherein said 10-dihydro-10-deoxo-11-azaerythromycin A of formula V is hydrolyzed in a mixture of a concentrated inorganic acid inthe present of an inert solvent.

12. The process of claim 11 wherein said hydrolysis is carried out by heating under reflux.

13. The process of claim 11 wherein said solvent is chloroform.

14. A method for the manufacture of 10-dihydro-10-deoxo-11-azaerythronolide A compounds of the formula (I)

wherein $R_1$ stands for a lower alkyl group, $R_2$, $R_3$, and $R_4$ each stands for a hydrogen atom and optionally pharmaceutically acceptable acid addition salts thereof, which comprises reacting 10-dihydro-10-deoxo-11-azaerythronolide A of the formula (III)

with aliphatic aldehydes of the formula $R_5$—CHO (IV)

wherein $R_5$ stands for hydrogen or a lower alkyl group, in the presence of formic acid or hydrogen in the presence of a noble metal catalyst.

15. The method of claim 14 wherein said compound III is reacted with a 1-3 equimolar excess of formaldehyde in the presence of at least the identical quantity of said formic acid in an inert solvent.

16. The method of claim 15 wherein said inert solvent is acetone and a halogenated hydrocarbon.

17. The method of claim 14 wherein said compound III is reacted with an aldehyde of formula IV with hydrogen in the presence of a noble metal catalyst.

18. The method of claim 17 wherein a 1-2 fold equimolar excess of said aldehyde and a 0.5 to equimolar quantity of said noble metal catalyst is employed.

19. The method of claim 7 which further includes subjecting the product obtained by said hydrolysis to acylation with lower aliphatic anhydride to obtain a 10-dihydro-10-deoxo-11-azaerythronalide A of said formula (1) wherein $R_1$ stands for a lower alkanoyl group, and R₂, R₃, and R₄ each stands for a hydrogen atom or a lower alkanoyl group.

20. The method of claim 19 which further includes converting said 10-dihydro-10-deoxo-11 azarythronalide A into a pharmaceutically effective acid addition salt.

21. The method of claim 7 which further includes converting said 10-dihydro-10-deoxo-11 azarythronalide A into a pharmaceutically effective acid addition salt.

22. The method of claim 14 which further includes subjecting the precedent obtained by said hydrolysis to acylation with lower aliphatic anhydride to obtain a 10-dihydro-10-deoxo-11-azaerythronalide A of said formula (1) wherein R₁ stands for a lower alkanoyl group, and R₂, R₃, and R₄ each stands for a hydrogen atom or a lower alkanoyl group.

23. The method of claim 22 which further includes converting said 10-dihydro-10-deoxo-11 azarythronalide A into a pharmaceutically effective acid addition salt.

24. The method of claim 14 which further includes converting said 10-dihydro-10-deoxo-11 azarythronalide A into a pharmaceutically effective acid addition salt.

25. Antiinflammatory compositions comprising an anti-inflammatory effective amount of a compound of the formula (I)

wherein R₁ stands for a hydrogen atom, a lower alkyl group or a lower alkanoyl group, R₂, R₃, and R₄ have identical or different meanings and each stands for a hydrogen atom or a lower alkanoyl group, and optionally pharmaceutically acceptable acid addition salts thereof.

26. The method of treating inflammations in humans and animals which comprises administering a pharmaceutically and anti-inflammatory effective amount of a compound of the formula (I)

wherein R₁ stands for a hydrogen atom, a lower alkyl group or a lower alkanoyl group, R₂, R₃, and R₄ have identical or different meanings and each stands for a hydrogen atom or a lower alkanoyl group, and optionally pharmaceutically acceptable acid addition salts thereof.

* * * * *